(12) United States Patent
Ramsing et al.

(10) Patent No.: US 8,633,017 B2
(45) Date of Patent: Jan. 21, 2014

(54) DEVICE, A SYSTEM AND A METHOD FOR MONITORING AND/OR CULTIVATION OF MICROSCOPIC OBJECTS

(75) Inventors: Niels B. Ramsing, Risskov (DK); Jorgen Berntsen, Viborg (DK); Jens K. Gundersen, Viby J. (DK); Holger Soe Plougsgaard, Ega (DK)

(73) Assignee: Unisense FertiliTech A/S, Aarhus N (DK)

( * ) Notice: Subject to any disclaimer, the term of this patent is extended or adjusted under 35 U.S.C. 154(b) by 767 days.

(21) Appl. No.: 12/666,163

(22) PCT Filed: Jun. 27, 2008

(86) PCT No.: PCT/DK2008/050162
§ 371 (c)(1),
(2), (4) Date: May 10, 2010

(87) PCT Pub. No.: WO2009/003487
PCT Pub. Date: Jan. 8, 2009

(65) Prior Publication Data
US 2011/0165609 A1 Jul. 7, 2011

(30) Foreign Application Priority Data
Jun. 29, 2007 (DK) .......................... PA 2007 00952

(51) Int. Cl.
*C12M 1/34* (2006.01)
(52) U.S. Cl.
USPC ..................................... 435/288.4; 435/289.1
(58) Field of Classification Search
USPC .......... 435/252.1, 286.2, 288.4, 289.1, 303.1, 435/325
See application file for complete search history.

(56) References Cited

U.S. PATENT DOCUMENTS

| | | |
|---|---|---|
| 3,618,734 A | 11/1971 | Khan |
| 4,649,114 A | 3/1987 | Miltenburger et al. |
| 4,724,543 A | 2/1988 | Klevecz et al. |
| 4,894,343 A | 1/1990 | Tanaka et al. |
| 4,895,805 A | 1/1990 | Sato et al. |
| 5,196,168 A | 3/1993 | Muszak et al. |

(Continued)

FOREIGN PATENT DOCUMENTS

| | | |
|---|---|---|
| CN | 1502412 | 6/2004 |
| DE | 100 17 192 A1 | 10/2001 |

(Continued)

OTHER PUBLICATIONS

Holm et al., 1998, "Developmental kinetics of the first cell cycles of bovine in vitro produced embryos in relation to their in vitro viability and sex", Theriogenology, vol. 50, pp. 1285-1299.

(Continued)

*Primary Examiner* — Michael Hobbs
(74) *Attorney, Agent, or Firm* — Gifford, Krass, Sprinkle, Anderson & Citkowski, P.C.

(57) ABSTRACT

The present invention relates to a device, a system and a method for performing monitoring and/or cultivation of microscopic objects. Microscopic objects are in particular microscopic organisms like bacteria and cell cultures, such as cultivation objects like tissue samples and embryos, providing optimal and safe cultivation conditions for incubation during embryo development and for facilitating the selection of optimal embryos to be used in in vitro fertilization (IVF) by facilitating embryo handling for automated digital imaging and time-lapse microscopy.

20 Claims, 5 Drawing Sheets

(56) References Cited

U.S. PATENT DOCUMENTS

| | | | |
|---|---|---|---|
| 5,652,142 | A | 7/1997 | Barker et al. |
| 5,763,279 | A | 6/1998 | Schwarz et al. |
| 5,968,340 | A | 10/1999 | Land et al. |
| 6,228,636 | B1 | 5/2001 | Yahiro et al. |
| 6,391,577 | B1 | 5/2002 | Mikkelsen et al. |
| 6,434,320 | B1 | 8/2002 | Myers et al. |
| 6,730,471 | B1 | 5/2004 | Katerkamp et al. |
| 7,336,401 | B2 | 2/2008 | Unal et al. |
| 7,724,937 | B2 | 5/2010 | So et al. |
| 2002/0072113 | A1 | 6/2002 | Barbera-Guillem et al. |
| 2003/0138942 | A1 | 7/2003 | Cecchi et al. |
| 2003/0185450 | A1 | 10/2003 | Garakani et al. |
| 2004/0147012 | A1 | 7/2004 | Yokoi et al. |
| 2004/0180428 | A1 | 9/2004 | Takeshita et al. |
| 2005/0041102 | A1 | 2/2005 | Bongiovanni et al. |
| 2005/0118563 | A1 | 6/2005 | Sher et al. |
| 2005/0205673 | A1 | 9/2005 | Morris et al. |
| 2006/0057710 | A1 | 3/2006 | Ishiura et al. |
| 2006/0201883 | A1* | 9/2006 | Hofmeister et al. ......... 210/649 |
| 2007/0015289 | A1* | 1/2007 | Kao et al. ................ 436/180 |
| 2007/0161106 | A1* | 7/2007 | Jervis et al. ................ 435/325 |
| 2008/0056952 | A1* | 3/2008 | Angros ...................... 422/99 |

FOREIGN PATENT DOCUMENTS

| | | |
|---|---|---|
| DK | PA 2005 01438 | 4/2007 |
| EP | 0 311 059 A | 4/1989 |
| EP | 0 448 923 | 11/1990 |
| EP | 1 041 154 | 12/1995 |
| EP | 1 134 583 | 3/2000 |
| EP | 1 531 422 | 5/2005 |
| EP | 1 542 154 | 6/2005 |
| EP | 1 595 041 A | 11/2005 |
| EP | 1 916 296 | 4/2008 |
| GB | 1 426 786 | 9/1973 |
| JP | H02-171866 | 7/1990 |
| JP | 2001-330582 | 11/2001 |
| JP | 2002-122568 | 4/2002 |
| JP | 2002262856 A | 9/2002 |
| JP | 2004166554 A | 6/2004 |
| JP | 2004528020 A | 9/2004 |
| JP | 2005/168341 | 6/2005 |
| JP | 2006014675 | 1/2006 |
| JP | 2006/034256 | 2/2006 |
| JP | 2006280298 A | 10/2006 |
| RU | 2187111 | 8/2002 |
| WO | WO 8705114 | 8/1987 |
| WO | WO 91/06628 | 5/1991 |
| WO | WO 92/20359 A | 11/1992 |
| WO | WO 97/19345 | 5/1997 |
| WO | WO 98/05753 | 2/1998 |
| WO | WO 98/21309 | 5/1998 |
| WO | WO 2000/44876 | 8/2000 |
| WO | WO 00/58437 | 10/2000 |
| WO | WO 01/02539 | 1/2001 |
| WO | WO 01/02598 | 1/2001 |
| WO | WO 01/23886 | 4/2001 |
| WO | WO 01/26609 | 4/2001 |
| WO | WO 02/45018 | 6/2002 |
| WO | WO 03/077552 | 9/2003 |
| WO | WO 2004/056265 | 7/2004 |
| WO | WO 2005/030986 | 4/2005 |
| WO | WO 2005/039181 | 4/2005 |
| WO | WO 2007/042044 | 4/2007 |
| WO | WO-2007049078 A1 | 5/2007 |
| WO | WO 2007/144001 | 12/2007 |
| WO | WO 2007/145196 | 12/2007 |
| WO | WO 2007/145198 | 12/2007 |
| WO | WO 2009/003487 | 1/2009 |

OTHER PUBLICATIONS

Lundin et al., 2001, "Early embryo cleavage is a strong indicator of embryo quality in human IVF", Human Reproduction, vol. 16, No. 12, pp. 2652-2657.

Overstrom, Eric W., 1996, "In vitro assessment of embryo viability", Theriogenology, vol. 45, pp. 3-16.

Beliën et al., 1997, "Counting mitoses by image processing in feulgen stained breast cancer sections: The influence of resolution". Cytometry 28, pp. 135-140.

Bhattacharya et al., 2004, "What is the most relevant standard of success in assisted reproduction? Redefining success in the context of elective single embryo transfer: evidence, intuition and financial reality", Human reproduction pp. 1-4.

Biran et al: "Optical imaging fiber-based single live cell arrays: a high density cell assay platform", Anal. Chem. 2002, vol. 74, pp. 3046-3054.

Bos-Mikich et al., 2001, "Early cleavage of human embryos: an effective method for predicting successful IVF/ICSI outcome", Hum Reprod 16, pp. 2658-2661.

Curl et al., 2004, "Quantitative phase microscopy: a new tool for measurement of cell culture growth and confluency in situ". Pflugers Arch—Eur J Physiol 448, pp. 462-468.

Eccles et al., 1986, "Automatic digital image analysis for identification of mitotic cells in synchronous mammalian cell cultures". Pubmed, anal quant cytol histol 8: pp. 138-147.

ESHRE position paper on the EU Tissues and Cells Directive EC/2004/23, Nov. 2007.

Fenwick et al., 2002, "Time from insemination to first cleavage predicts developmental competence of human preimplantation embryos in vitro", Hum reprod 17, pp. 407-412.

Gonzales et.al., 1995, "Prediction of the development potential of hamster embryos in vitro by precise timing of the third cell cycle", Journal of ReproduCtion and Fertility, vol. 105, No. 1, pp. 1-8.

Grenier Microplate Dimensions Guide (2007), Compendium of Greiner Bio-One Microplates.

Grisart et.al., 1994, "Cinematographic analysis of bovine embryo development in serum-free oviduct-conditioned medium", Journal of Reproduction and Fertility, vol. 101, No. 2, pp. 257-264.

Haney et al., 2001, "Tracking tumor growth rates in Patients with Malignant gliomas: A test of two algorithms". AJNR An J Neuroradiol 22, pp. 73-82.

Hnida et al: Computer-controlled, multilevel, morphometric analysis of blastomere size as biomarker of fragmentation and multinuclearity in human embryos. Human Reproduction, vol. 19, No. 2, Feb. 2004, pp. 288-293.

Holm et al., 2002, "Kinetics of early in vitro development of bovine in vivo-and in vitro-derived zygotes produced and/or cultured in chemically defined or serum-containing media", Reproduction 123, pp. 553-565.

Holm et al., 2003 "Developmental kinetics of bovine nuclear transfer and parthenogenetic embryos", Cloning and stem cell, vol. 5 No. 2, pp. 133-142.

Houghton et al., 1996, "Oxygen Consumption and Energy Metabolism of the Early Mouse Embryo", Molecular reproduction and development 44, pp. 476-485.

Jung et al., 1999, "Oxygen microsensor and its application to single cells and mouse pancreatic islets", Anal. Chem., 71, 3642-3649.

Lane et al., 1996, "Selection of viable mouse blastocysts prior to transfer using a metabolic criterion", Human Reproduction vol. 11, No. 9, pp. 1975-1978.

Lequarre et.al., 2003, "Cell cycle duration at the time of maternal zygotic transition for in vitro produced bovine embryos: Effect of oxygen tension and transcription inhibition", Biology of Reproduction, vol. 69, No. 5, pp. 1707-1713.

Magnusson et al., 1986, "Oxygen consumption by human oocytes and blastocysts grown in vitro", Human Reproduction vol. 1 No. 3 pp. 183-184.

Majerus et al., 2000, "Characterization of embryos derived from calf oocytes: Kinetics of cleavage, cell allocation to Inner cell mass, and trophectoderm and lipid metabolism", Molecular reproduction and development 57, pp. 346-352.

Motosugi et al., 2005, "Polarity of the mouse embryo is established at blastocyst and is not prepatterned", Genes & development 19, pp. 1081-1092.

Neuber et al., 2003, "Sequential assessment of individually cultured human embryos as an indicator of subsequent good quality blastocyst development", Human Reprod vol. 18, pp. 1307-1312.

(56) References Cited

OTHER PUBLICATIONS

Oberholzer et al., 1996, "Methods in quantitative image analysis". Histochem Cell Boil 105, pp. 333-355.

Petersen et al., 2001, "Embryo selection by the first cleavage parameter between 25 and 27 hours after ICS"I. J Assist Reprod Genet 18, vol. 4, pp. 209-212.

Sakkas et al., 1998, "Early cleavage of human embryos to the two-cell stage after intracytoplasmic sperm injection as an indicator of embryo viability", Hum Reprod 13, pp. 182-187.

Sakkas et al., 2001, "Assessment of early cleaving in vitro fertilized human embryos at the 2-cell stage before transfer improves embryo selection", Fertil Steril 76, pp. 1150-1156.

Salumets et al., 2002, "The predictive value of pronuclear morphology of zygotes in the assessment of human embryo quality", Hum Reprod 16, pp. 2177-2181.

Schatten et.al., 2005, "The significance of mitochondria for embryo development in cloned farm animals", Mitochondrion, Elsevier, Amsterdam, NL, vol. 5, No. 5, pp. 303-321.

Shiku et al., 2001, "Oxygen Consumption of Single Bovine Embryos Probed by Scanning Electrochemical Microscopy", Anal. Chem., 73, pp. 3751-3758.

Shoukir et al., 1997, "Early cleavage of in-vitro fertilized embryos to the 2-cell stage: a novel indicator of embryo quality and viability". Hum Reprod 12, pp. 1531-1536.

Squirrell et.al., 1999, "Long-term two-photon fluorescence imaging of mammalian embryos without compromising viability", Nature Biotechnology, Nature Publishing Group, vol. 11, No. 17, pp. 763-767.

Squirrell et.al., 2003, "Imaging mitochondrial organization in living primate oocytes and embryos using multiphoton microscopy", Microscopy and Microanalysis, Springer, New York, vol. 9, No. 3. pp. 190-201.

Tokura et.al., 1993, "Sequential observation of mitochondrial distribution in mouse oocytes and embryos", Journal of Assisted Reproduction and Genetics, vol. 10, No. 6, pp. 417-426.

Trettnak et al., 1998, "Optical oxygen sensor instrumentation based on the detection of luminescence lifetime", Adv. Space Res. vol. 22, No. 10, pp. 1465-1474.

Trimarchi et al., 2000, "Oxidative phosphorylation-dependent and -independent oxygen consumption by individual preimplantation mouse embryos", Biol. Reprod., 62, 1866-1874.

Van Blerkom et.al., 2001, "A microscopic and biochemical study of fragmentation phenotypes in stage-appropriate human embryos", Human Reproduction, vol. 16, No. 4, pp. 719-729.

Vayena et al., 2001, "Current practices and controversies in assisted reproduction": Report of a meeting on "Medical, Ethical and Social aspects of assisted reproduction" held at WHO headquarters in Geneva, Switzerland.

Windt et al., 2004, "Comparative analysis of pregnancy rates after the transfer of early dividing embryos versus slower dividing embryos", Hum Reprod vol. 19 No. 5 pp. 1155-1162.

Wodnicka et al., 2000, "Novel fluorescent technology platform for high throughput cytotoxicity and proliferation assays", Jour. Biomol. screening, 5, 3, 141-152.

Wong et al., 2002, "Non-invasive imaging of human embryos before embryonic genome activation predicts development to the blastocyst stage", Nature Biotechnology, vol. 28, No. 10, pp. 1115-1124.

Baltz et al., 1991, "Oxygen transport to embryos in microdrop cultures", Molecular Reproduction and Development, vol. 28, pp. 351-355.

Harqittai et al., 1987, "A pyrene fluorescence technique and microchamber for measurement of oxygen consumption of single isolated axons", Analytical Biochemistry, vol. 163, pp. 418-426.

Howland et al., 1931, "A method for determining the oxygen consumption of a single cell", Col. 14, No. 3, pp. 339-348.

Matsubara, S. et al., Analysis of Endoglin Expression in Normal Brain Tissue and in Cerebral Arteriovenous Malformations, *Stroke*, 31: 2653-60, 2000.

\* cited by examiner

DEVICE, A SYSTEM AND A METHOD FOR MONITORING AND/OR CULTIVATION OF MICROSCOPIC OBJECTS

CROSS-REFERENCE TO RELATED APPLICATIONS

This application is the U.S. national phase of PCT/DK2008/050162 filed Jun. 27, 2008, which claims priority of Danish Patent Application No. PA 2007 00952 filed Jun. 29, 2007.

The present invention relates to a device, a system and a method for performing monitoring and/or cultivation of microscopic objects. Microscopic objects are in particular microscopic organisms like bacteria and cell cultures, such as cultivation objects like tissue samples and embryos, providing optimal and safe cultivation conditions for incubation during embryo development and for facilitating the selection of optimal embryos to be used in in vitro fertilization (IVF) by facilitating embryo handling for automated digital imaging and time-lapse microscopy.

BACKGROUND

Manual positioning of small objects for microscopy is time-consuming. Finding an object, placing it centrally in the field of view and focusing on the features of interest accounts for a significant part of the workload associated with clinical microscopy. A particular case of interest is microscopy of oocytes and embryos as part of a standard IVF treatment where handling of the embryo outside the safe incubator environment with defined temperature, atmosphere and pH is a significant stress factor that must be minimized. Automated systems are known, which are able to re-position objects efficiently by seeking out predefined X-Y-Z coordinates where the object of interest is deemed to be positioned. However the initial task of obtaining the correct coordinates for a given object is very time-consuming. If object movement and image acquisition is automated, it usually implies acquiring consecutive images in a grid pattern and stitching these together in a collage to enable search algorithms or the human operator to find the object of interest. Alternatively it involves the assistance of an operator to locate the object manually and record the coordinates.

While it is generally possible to position larger objects in predefined spots where they remain stationary, this becomes increasingly difficult with objects of microscopic sizes in a liquid media. An example of particular interest is early human embryos, which are only about ⅛ mm in diameter (approx. 120 μm) with a density slightly higher than their growth medium. Positioning embryos accurately in media droplets is difficult, and handling easily disturbs their position.

The exact positioning of a microscopic object is of general interest in many applications. However, when using Embryo Transfer (ET) techniques, such as IVF (In Vitro Fertilization) and related techniques, this involves in vitro culturing of the developing embryo for a period of days before re-implantation of selected embryos. Even with the ideal growth conditions, selection criteria are needed as a tool to choose the most viable embryos for re-implantation. The viability of an embryo is an important parameter in order to determine the embryos suitability for transfer. At a practical level, precise positioning for microscopy is a prerequisite for assessing the viability of the embryo following manipulation. In practice, embryo evaluation is limited to a more or less subjective grading based on morphological criteria. The respiration rate of the embryo may prove a good candidate for an objective viability indicator. Therefore, a need exists for a fast, simple and non-disturbing method, system and device for enabling morphological evaluation and/or possibly measurement of individual embryo respiration rates as a measure for the embryo viability.

WO 01 02539 describes a well within a well (WOW) approach to provide individual cell cultures in microscopy slides, an advantage thereof as stated is providing a small volume well within a larger volume well for enabling a better culturing environment for each individual embryo.

However, manual and/or automatic handling of the microscopy slide comprising said WOW have proven to be time consuming and difficult, because it is practise has proven to be difficult to insert an embryo or other cell culture in the smaller volume well. Further if one was to provide more than one WOW upon a slide there may be a risk of contamination from one WOW to another WOW, which may be detrimental to cell growth. One problem in particular being that if one cell culture experiences lysis or other developmental problems, a contamination or spread of cell lysate from one well to another may propagate such problem.

Another problem with known microscopy slides, e.g. comprising at least one WOW, for culturing purposes is how to maintain a stable environment for developing said living cell cultures, i.e. keeping a relatively stable predetermined temperature, a stable gas composition, a sufficient amount of culturing media, the required humidity, and reduce the risk of contamination from the surroundings, and other environmental influences.

Further, even though a more accurate positioning of individual objects may be provided using WOW devices due to the fact that a relatively determined coordinate set in both the x, y and z direction may be accomplished within said slide; in view of the manipulating problems stated above, the use of a WOW device may reduce the handling time, but not significantly, nor does it protect against mutual and external contamination.

When applied to embryo viability assessment, the miscoscopy method, device and system according to the system should be providing the following key elements as outlined by Overström 1996 (see In vitro assessment of embryo viability. Theriogenology 45:3-16 1996): 1) The ability to make simultaneous objective measurements of multiple individual embryos, 2) The sensitivity and resolution to measure individual embryos/oocytes, 3) Rapid evaluation i.e. ~30 min or less, 4) Viability test must be non-perturbating and ideally non-invasive, 5) Technically simple and user friendly. 6) Reduced cost when acquiring and handling.

On the above background it is one purpose of the present invention to provide a method, a device and a system of the initially mentioned type, which reduces the above mentioned disadvantages of the know methods, devices and systems.

SUMMARY OF THE INVENTION

The purpose of the present invention is to culture microscopic organisms, to provide suitable, stable living conditions during incubation and additionally facilitate handling, observation and maintenance. The present invention greatly facilitates placing microscopic objects in defined spots that can be routinely inspected, manipulated and/or imaged automatically.

The above mentioned purpose is fulfilled with a method, a device and/or a system according to the various aspects of the invention as described herein.

In a first aspect the invention relates to a device for monitoring and/or culturing of at least two microscopic objects and object media, comprising a slide comprising at least two depressions in a top surface thereof;
wherein each depression comprising an indent of a smaller cross section than the depression for holding each respective microscopic object and object media,
said slide being provided with a reservoir for providing a common overlaying layer (7) between said depressions in such a way that said media is not in mutual fluid communication, and/or
wherein each depression comprising an indent of a smaller cross section than the depression for holding each respective microscopic object and object media,
wherein at least said depression and/or said indents exhibit a bottom surface profile corresponding to the contours thereof upon said slide; the topography of which profile being adapted for matching a corresponding topography of a slide holder, and/or
wherein each depression comprising an indent of a smaller cross section than the depression for holding each respective microscopic object and object media,
wherein at least a part of said device is provided with a handling protrusion, and/or
wherein said slide comprises means for uniquely identifying each depression.

The provision of an indent within a depression will automatically position the microscopic object in a predefined spot by letting it slide down a slope to settle in the small indent, e.g. with a flat bottom, which is suited for microscopy. The indent ensures that subsequent handling does not perturb the position of the object within the microscopy slide. Accordingly, automatic density driven positioning of microscopic objects, such as living organisms is provided in a central indent within the depression. The central indent constitutes a reservoir that can easily be detected, e.g. by automated image analysis algorithms, so that unattended automated microscopy of the object within the reservoir can be performed. Preferably, the sides of the well leading to the reservoir are sloping in order for improving the probability of finding the object inside the smaller sized indent within the much larger sized depression.

Providing more than one indent upon one slide reduces handling time because observations or images may be made without having to remove the slide and insert a new one for each new object to be observed.

In a second aspect the invention relates to a system arranged for performing monitoring and/or culturing of at least two microscopic objects comprising a device for handling at least two microscopic objects and object media, said device comprising a slide comprising at least two depressions in a top surface thereof; each depression comprising an indent of a smaller cross section than the depression for holding each respective microscopic object and object media, wherein at least said indents exhibit a bottom surface profile corresponding to the contours thereof upon said slide; wherein said system is further provided with positioning means comprising a slide holder, which is adapted for matching said bottom surface profile at least corresponding to the contours of at least said at least two indents.

In a third aspect the invention relates to a method for handling a device as defined above, comprising the step of positioning said device within a system as defined above by matching said bottom surface profile of said device at least corresponding to the contours of at least said at least two indents to corresponding positioning means comprising a slide holder of said system.

Said indent, device, system and method described is in particular suitable for performing embryo oxygen respiration rate sensor probing using any type of glass capillary devices, systems and methods available.

SHORT DESCRIPTION OF DRAWINGS

In the following, the invention will be described in more detail with reference to some embodiments illustrated in the schematic not-to-scale drawings, where like numerals indicate the same features, in which.

Figure 12:
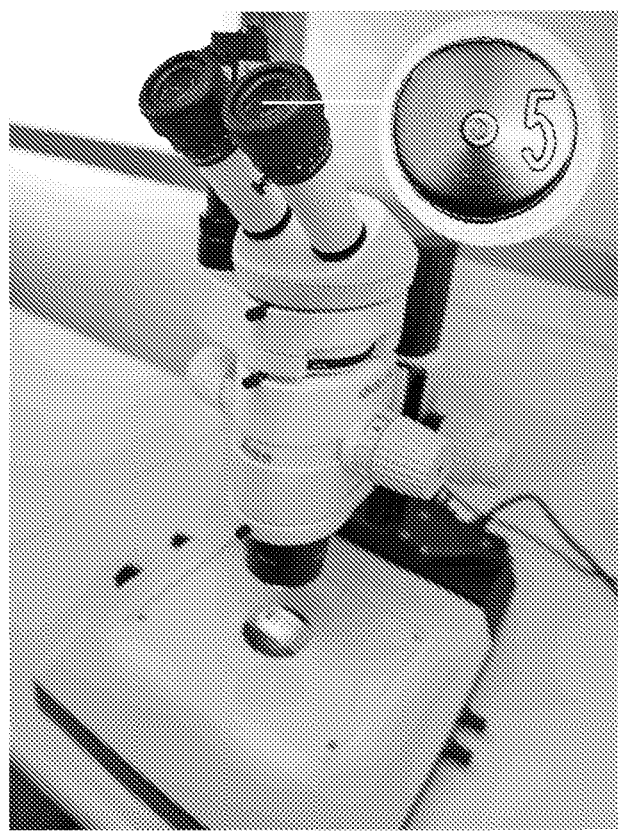

FIG. 12 Well ID number with micronumerals that can easily be observed during handling in a dissection microscope. The number "5" is about 1. mm high, and 0.4 mm wide.

DETAILED DESCRIPTION OF EMBODIMENTS

Figures 1A, 1B:
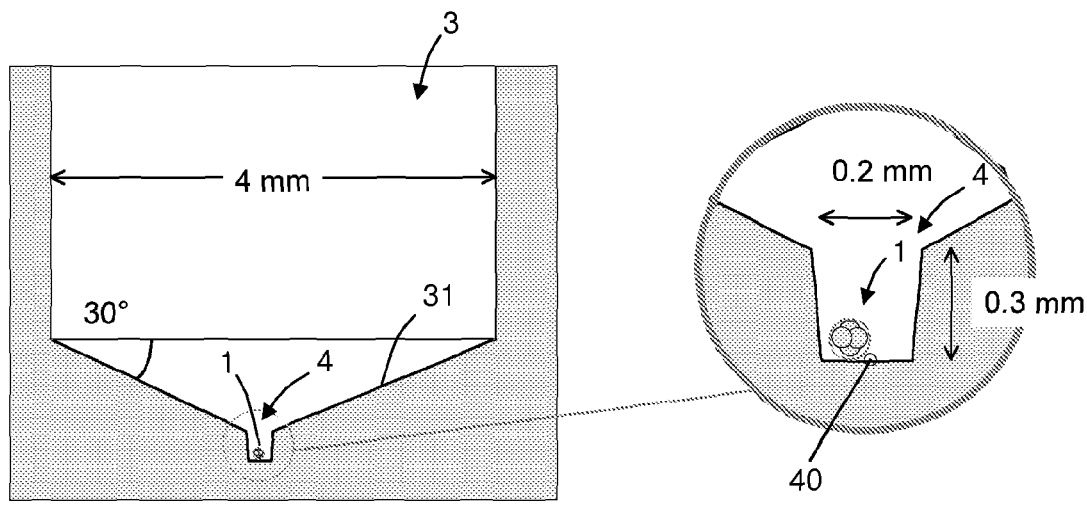
FIG. 1A, 1B is a side view of a depression containing an indent for a device according to an embodiment of the invention for culturing and/or monitoring embryos, and a detail view of the indent comprising said embryo in a device of FIG. 1.

In FIG. 1A is shown a side cut view of a slide or device in a depression containing an indent for a device according to an embodiment of the present invention, and in FIG. 1B is shown a detail view of the indent of FIG. 1A holding a microscopic object, e.g. an embryo. The depressions and device is in particular suited for density based positioning of embryos for monitoring and/or culturing in an embryo culturing and/or microscopy slide.

Said microscopic object may be microscopic organisms, such as growing cell cultures, and said device is in particular suitable for handling, microscoping and/or culturing developing embryos. Said microscopic object may be part of a larger or smaller sized object, e.g. smaller or larger than the diameter of the indent. The term "microscopic object" is defined as an object whose largest dimension is less than 2 mm, preferably less than 1 mm, preferably less than 500 µm, most preferably less than 200 µm.

An embryo 1 is approximately spherical and is composed of one or more cells (blastomeres) surrounded by a gelatine-like shell, an acellular matrix known as the zona pellucida. The zona pellucida performs a variety of functions until the embryo hatches, and is a good landmark for embryo evaluation. The zona is spherical and translucent, and should be clearly distinguishable from cellular debris.

An embryo is formed when an oocyte is fertilized by fusion or injection of a sperm cell or spermatozoa. The term is traditionally used also after hatching, which comprises rupture of zona pelucida and the ensuing implantation. For humans the fertilized oocyte is traditionally called an embryo for the first eight weeks. After that i.e. after eight weeks and when all major organs have been formed it is called a foetus. However the distinction between embryo and foetus is not generally well defined.

The slide or device surface is provided with at least one media filled depression 3 in the upper surface of said device said depression preferably being cylindrical, such as a depression having a diameter of around 4.0 mm, which may vary from 1 to 25 mm depending on application. An embryo may be easily deposited into the depression using a standard IVF pipette because the diameter of the depression is much larger than the object of interest. The other dimensions of the depression, such as height and vertical and horizontal sectional shape are selected such that the microscopic object may be easily inserted into the depression. The embryo slowly descends to the bottom of the depression by ensuring that the surrounding growth medium density is slightly lower than the density of the embryo, and providing relatively smooth walls of said depression 3.

A substantially conical smooth bottom part or funnel 31 of the depression is provided, alternatively said funnel may be provided vertically sectioned in pyramidal, slit, wedge, trapezoid, or any other suitable shape, having angles of about 5 to 60 deg, generally 30 deg relative to vertical as shown in FIG. 1A. Accordingly, the embryo will by gravitational force and/or applied centrifugation roll into an indent 4 at the centre of the depression 3 and/or funnel 31, when it has reached a bottom part of the depression, i.e. above or within said funnel 31. The unattended loading process takes a few minutes when the media is having a relatively high viscosity. The small indent ensures that the embryo maintains its position despite handling movements.

A funnel may ease and guide the object of interest from the depression to the indent. The funnel is usually placed on the bottom of the depression to capture and position objects with a higher density than the surrounding medium. The preferably substantially smooth surfaced funnel may have angles of about 5 to 60 deg, preferably between 10 and 45 deg, more preferably 15 to 35 deg, most preferably 25 to 30 deg relative to horizontal.

The dimensions of the indent 4 is often selected to be relatively small compared to the diameter of the depression, and to the size of the object, approximately 1.1× to 10× the diameter of the object, preferably 1.5× to 3× the diameter of the object, so that the object position is well defined relative to the slide itself. Thus, high resolution images and monitoring can easily be acquired of the whole indent volume, if the slide position relative to said microscope is known. The indent is preferably provided with a substantially planar bottom surface 40 in order to ease monitoring and/or culturing of said embryo by microscopy or the like.

The optimal height of the indent 4 is determined by the need to keep the embryo 1 positioned despite handling movements. A deeper indent with higher walls will protect the embryo against bulk movement of the overlaying growth media. However, the embryo may be removed for transfer to the recipient patient after the end of the observation period. Thus, a shallower indent will favour easy embryo removal. A reasonable practical compromise appear to be an indent with a depth substantially similar to its width i.e. 0.5× to 10× the diameter of the embryo. As shown in FIG. 1B a depth of 0.3 mm and a diameter of 0.2 mm may be selected. The walls of the embryo indent are largely vertical, but may be slightly inclined in order to widen the opening of the indent and facilitate embryo removal, e.g. from 5 to 20 deg as shown on FIG. 1B. The indent may alternatively be formed cylindrical, box-shaped, conical, truncated or cone or the like, any suitable shape to hold the microscopic object, prevent accidental displacements by handling and environmental influences, and induced bulk flow of the medium. The smaller the dimensions of the indent the better the position of the microscopic object is defined. However, with very small indents it may be very difficult to remove the microscopic object from the indent at the end of the observation period.

In one embodiment the dimensions of an indent have substantially equal diameter and depth. Furthermore, said indents are preferably provided substantially centrally within their respective depression.

The dimensions of the slide are preferably such as to fit within a standard and/or specially adapted microscope system and/or cultivation system, such as 25×76 mm.

The vertical sectional cut of a depression and/or indent may hold the form of any of the group containing cylindrical, tapered, coned, slit-shaped, pyramidal, trapezoid, part-of-a-circle, or substantially circular. The horizontal sectional cut of a depression and/or indent may hold the form of any of the group containing circular, elliptic, rectangular, harlequin, or hexagonal.

Figure 2:
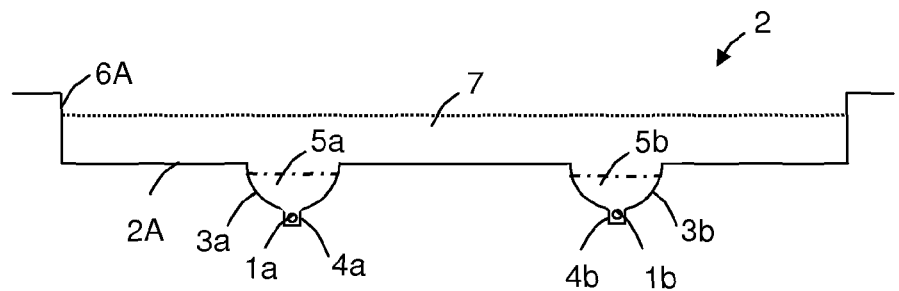
FIG. 2 is a side cut view of a detail of a device according a first embodiment of the present invention suitable for embryo incubation and examination.

In FIG. 2 is shown a device according to a first embodiment of the present invention. Said device comprises a microscopy slide 2 comprising a series i.e. at least two of said depressions 3a, 3b in a top surface 2A of the slide material. Each depression 3a, 3b comprises an indent 4a, 4b of a smaller cross section than the depression for receiving and holding each respective microscopic object 1a, 1b and object media 5a, 5b, each indent and/or depression e.g. of dimensions and/or form according to the above. Two microscopic objects, i.e. embryos 1a, 1b have been inserted into the microscopy slide 2, i.e. one into each of the indents 4a and 4b, respectively. Said object media 5a, 5b may be any suitable media for surrounding, holding and protecting said microscopic objects, such as a cell growth media for such embryo. Said media 5a may be different from or the same as said other media 5b, depending on application of the device.

Figure 3:
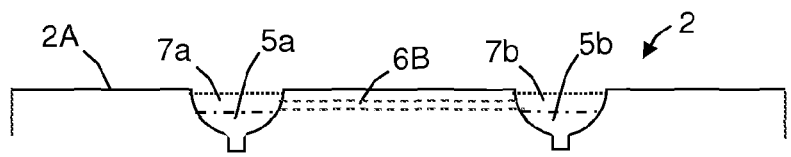
FIG. 3 is a side cut view of a detail of a device according to a second embodiment suitable for embryo incubation and examination.

As shown in FIGS. 2 and 3, said slide 3a, 3b is provided with a reservoir 6A, 6B for providing a common overlaying layer 7 between said depressions 3a, 3b in such a way that when an object media 5a, 5b is provided inside said depressions and/or indents media 5a is not in mutual fluid communication with media 5b. Thus, the risk during handling of said device of spilling over object media 5a, 5b between the different depressions and/or indents is reduced, which again reduces the introduction of adverse effects between said microscopic objects 1a, 1b, e.g. when the objects are embryos and the device is a culturing dish, and one of said embryos lyse. Further, movement of the device may induce minor bulk movement in the overlaying layer, but a significantly reduced movement within said object media, reducing movement of the embryo over time, which is in particular an advantage during microscopy and/or culturing of said objects. Further, by providing an overlaying layer upon said object medium, said object medium is better protected against detrimental environmental influences, such as temperature, humidity, and/or pressure variations, and the risk of contaminating the object and object media is further reduced.

As shown in FIG. 2 said reservoir is provided as a common recess 6B within said top surface 2A, which enables the formation of a common reservoir of an overlaying layer or top layer, e.g. of an immersion oil. As an alternative or as a supplement, as shown in FIG. 3, showing a second embodiment of said device, said reservoir is a fluid connection 6B, e.g. a channel or tube, open or closed, respectively, to the external surface, between said at least two depressions 3a, 3b. Accordingly, the total height of the slide for enabling housing the depressions and indents may be reduced.

Said slide 2 is provided with a reservoir 6 for providing a common overlaying layer 7 between said depressions 3a, 3b in such a way that said media 5a, 5b is not in mutual fluid communication.

Further, a shared immersion fluid reservoir, i.e. a common reservoir therefore provides for easy handling and incubation without the need for supplemental humidity control of the growth media. Also, the relatively large sized or deep immersion fluid reservoir separates the media in individual indents and/or depressions and reduces the risk of contamination from particles, gases in the surrounding air, etc.

Each microscopy slide contains a series of indents that each hold a single microscopic object, e.g. each indent contains an embryo from the same patient or different patients. By providing means for separating the medias in such a way that the media in each depression is kept without mutual communication this reduces the risk of media spill over from one depression and/or indent to another. Further, in particular, by providing Individual media compartments for each object, e.g. embryos, this may prevent contamination or adverse effects e.g. if one of the embryos or cell cultures in a nearby indent should lyse. As each organism is placed in a different indent containing media which are separated by e.g. an overlaying layer of immersion oil, it is highly unlikely that adverse compounds should be able to diffuse through the hydrophobic oil to neighbouring indents.

The object media is preferably filled into each of said depressions/indents in such a way, that the level at the top surface of said media 5a, 5b is not provided above the level of the transition from said depression to said reservoir 6, see FIGS. 2 and 3. Said media may be any suitable material, such as embryo growth media, other cell culture media, and the like. liquid, flexible, semi-rigid, or rigid media. Different medias for culturing cell population are known in the art. An example of culturing an embryo is described in PCT application No. WO 2004/056265.

Further, the overlaying layer of an immersion media such as a suitable oil having varying viscosities, such as liquid, flexible, semi-rigid, or rigid, may be provided at least covering the upper diameter of each indent or depression holding a microscopic object to be cultured and/or microscoped.

Said object media and/or overlaying layer may be provided in a material, whose viscosity and/or transparency and/or density is temperature variant, e.g. when heated to a culturing temperature, said media and/or layer is transparent and/or at least said layer is of a higher viscosity than said media, and/or said media is of a higher density than said layer.

Figure 4:
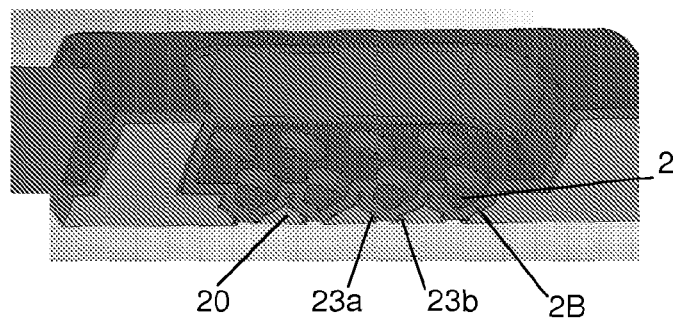
FIG. 4 is a side cut view of a detail of a device according to a third embodiment of the present invention.
Figure 6:
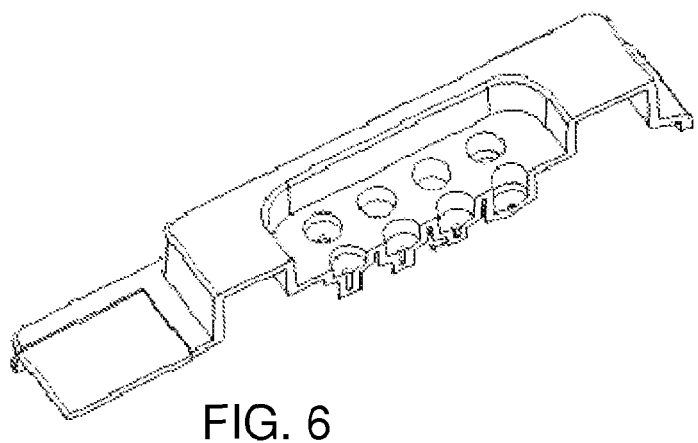
FIG. 6 is a perspective cut view along the section A-A shown in FIG. 5.

As shown in FIG. 4 the provision of said indents 4a, 4b and/or said depressions 1a, 1b and providing a relatively uniform slide material thickness overall, see FIGS. 4 and 6, results in the fact that the bottom surface 2B of the slide exhibiting a bottom surface profile 20 corresponding to the contours of at least said indents and/or depressions upon said slide 2. This is an advantage, when the device is inserted into a slide holder having a corresponding upper surface contour relative to said bottom surface profile 20 such as may be provided in e.g. a culturing and/or microscopy system, as will be discussed further below, in connection to FIG. 10. One or more devices according to the invention may be provided with the same unique bottom topography for cooperation with a large scale system comprising more than one device and/or being adapted for interchanging one or more of said devices over time.

Thus, in one embodiment the non-planar bottom surface profile of the cultivation slide matches the contours of a optionally heated aluminium holder which holds the slide so that the indents are inserted into depressions in the aluminium holder.

As shown in FIG. 4, in an embodiment of the device at least part of said profile 20 is provided with a heat conducting layer 23a, 23b, preferably at least forming part of a bottom surface of said indents. Thus, when arranging said device for connection to a heat source, a controlled thermostated environment for the embryos may be provided and maintained over extended time periods, which reduces the necessity for performing a fast analysis of said embryos and eases handling thereof. Said heat conducting layer may be a metal such as aluminium or steel Preferably, said heat conducting layer 23 is adapted for connection to a heat source, e.g. as may be provided in a cultivator and/or microscopy instrument.

In FIG. 4, said heat conductive layer 23a and 23b is provided upon the bottom surface profile along the substantially planar bottom surface of the indents, and ensures that the embryo is surrounded by a heat providing environment. Alternatively or as a supplement, said layer 23 is provided surrounding the bottom surface profile of the walls of said indent, The device comprises a disposable cultivation slide with depressions that contain the organisms in a suitable medium.

Alternatively or as a supplement, said heat conducting layer 23 provides at least part of the upper surface 2A of the slide 2, preferably at least part of the inner surfaces of the indents 4a, 4b and/or the depressions 3a, 3b.

The bottom part of the indent and/or said heat conductive layer is preferably planar and transparent, e.g. by providing said heat conductive layer 23a, 23b being provided with through passing suitably arranged holes to ensure an unobstructed monitoring of the embryo from below or above using e.g. standard or reversed microscopy and/or image acquisition and/or analysis.

Figure 5:
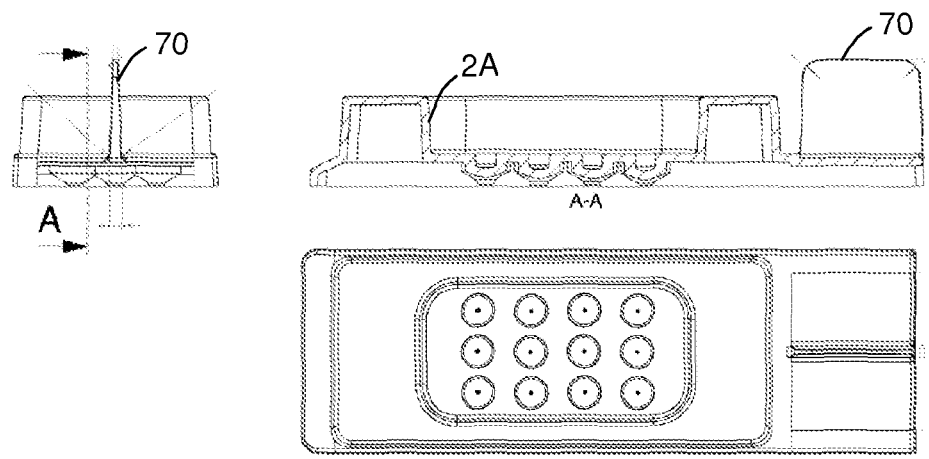
FIG. 5 is a technical drawing of a device of FIG. 4, further comprising a handling protrusion.

As shown in FIG. 5 a part of said device is provided with a handling protrusion (70), said part being a suitable position and extent within said top surface 2A; alternatively or as a supplement said part being said bottom part 2B. Providing said handling protrusion on a side part of said slide is possible. A device wherein at least part of said handling protrusion 70 is extending vertically upwards and/or downwards from said slide. Said handling protrusion 70 may preferably comprise a fin, e.g. provided with further extension or extensions than the side of the slide, wherein said handling protrusion 70 is provided in a heat conducting material and/or a polymer material.

Preferably, said handling protrusion 70 is arranged for providing identification labelling thereupon (not shown).

By arranging a handling protrusion the invention provides means for easy handling and insertion of slide without any contamination risk. The handling protrusion is especially important when the slide is placed in the slide holder. In one embodiment, due to the matching contours of the slide holder and the slide bottom the slide must be inserted vertically in the slide holder. This is difficult without a good grip on the slide.

In a preferred embodiment the handling protrusion does not interfere with a lid, and touching the handling protrusion does not constitute a contamination risk as would handling the slide by touching the sides in general.

As shown in FIG. 6, there is in the device provided a series of depressions 3a, 3b, wherein said depressions (3a, 3b) are mutually equidistantly positioned in at least one direction, eases positioning measurements performed thereupon and handling during monitoring/culturing.

Figure 7:
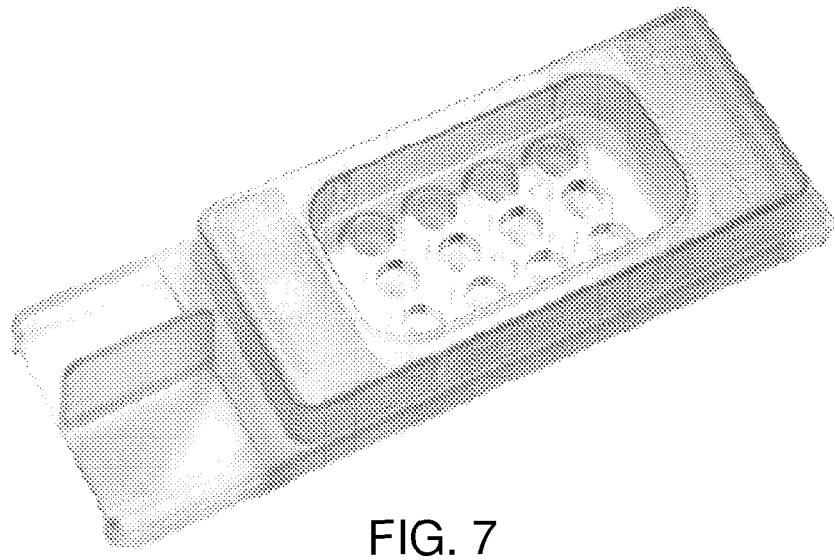
FIG. 7 is a perspective image of a device of FIGS. 4, 5 and 6, made in a transparent polymer material.

As shown in FIG. 7 at least part of the inner surfaces of said indents 4a, 4b and/or said depressions (3a, 3b) are made of a polymer, preferably substantially the entire microscopy slide 2 is made of a polymer, wherein said polymer may be a polyester, such as PEN, PETg, and/or PET, having a low embryotoxicity that may be ascribed to a high degree of internal immobilization of cytotoxic compounds within the polymer.

As shown in FIG. 7 there is further provided individual indent identification 41 in and/or upon said substantially planar bottom surface of the indent and/or in and/or upon said bottom surface profile and/or within said transparent bottom part of said indent, which preferably is visible in higher resolution such as during microscopy, in particular reverse microscopy.

Figure 8:
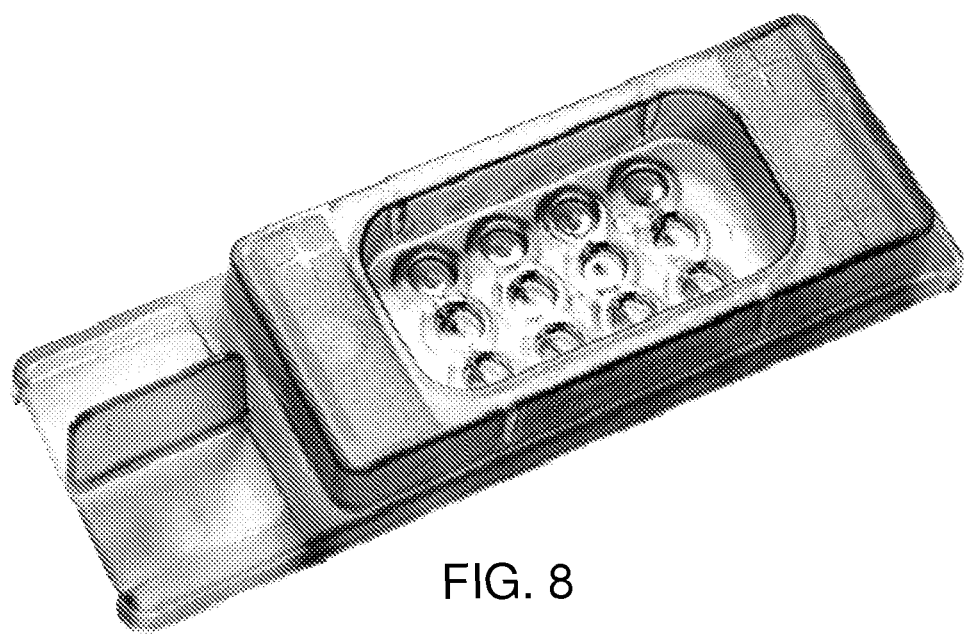
FIG. 8 is a perspective image of a device of FIGS. 4, 5 and 6, further comprising a heat conductive layer in aluminium provided at part of the bottom surface profile, i.e. the reverse contours of the depressions, indents and reservoir provided therein.

FIG. 8 is a slide or device provided with a great conducting material such as aluminium.

Figure 9:
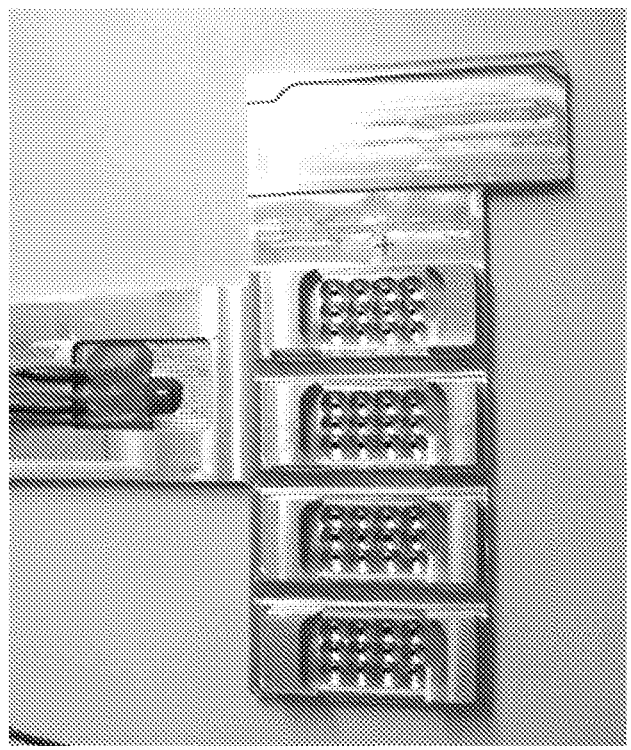
FIG. 9 is an image of a heat source suitable for cooperation with a system according to a first embodiment of the invention.

FIG. 9 is a laboratory test setup of a slide holder arm of aluminium, adapted for holding four separate slides or devices.

The device slide is preferably adapted to be placed in a system, which provides a stable environment for the organisms (temperature, gas composition, humidity etc.) and enable unattended monitoring of the organism by photography, measurement of metabolism etc.

1) The System Preferably Provides
   a. Temperature control through matching contours of aluminium holder in instrument and the inserted slide. The organism residing in each well is thus surrounded by heat conducting metal and therefore in a controlled environment.
   b. The tight fit between the matching contours of the slide and the slide holder ensure easy positioning of slide with µm accuracy as it settles in holder. Unattended microscopy is therefore possible even after removal and re-insertion of the slide.
   c. The automatic positioning of embryo AND slide is a prerequisite for automatic acquisition of time-lapse images.

Figure 10:
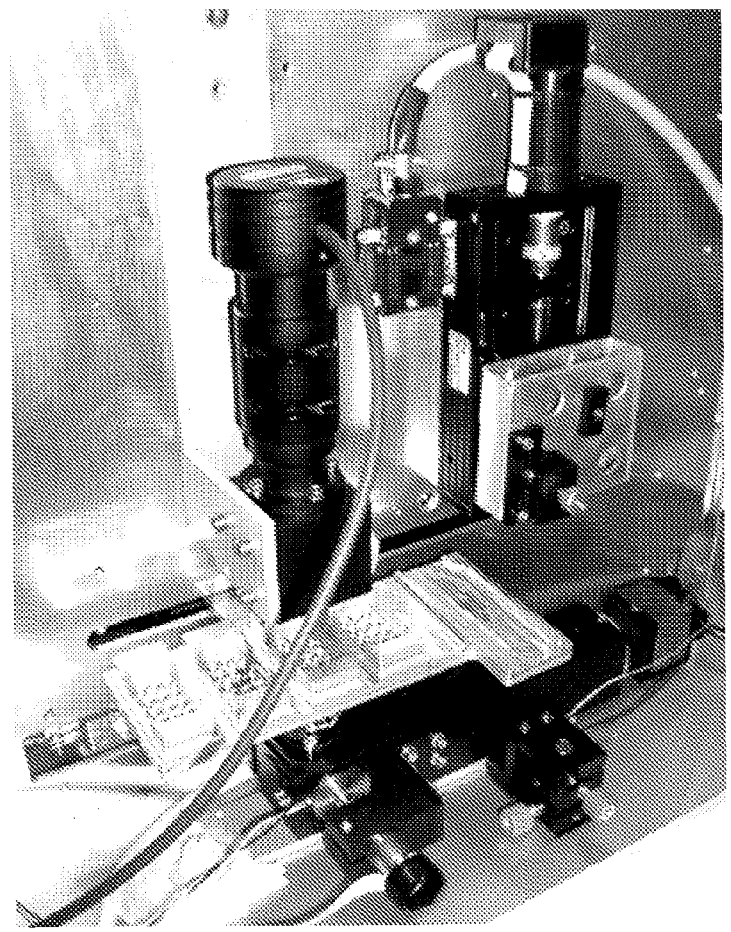
FIG. 10 is an image of a system according to a first embodiment of the invention.

As shown in FIG. 10, the invention further relates to a system arranged for performing microscopy and/or culturing of at least two microscopic objects 1a, 1b, comprises a device according to the invention as described above and also positioning means for holding said device. Preferably a microscope and said positioning means are arranged for positioning the device under the microscope or relative thereto. Said system may further comprise a heat source suitable for providing temperatures for culturing said at least two microscopic objects (1a, 1b) and said positioning means being arranged for positioning the device relative to said heat source. Said positioning means comprises a slide holder, which preferably is adapted for matching said bottom surface profile at least corresponding to the contours of at least said at least two indents, and may be provided as a slide holder in a culturing and/or monitoring system for manual and/or automatic monitoring and analysation The system may further be provided with a heat conducting layer adapted for providing a given stable temperature to at least said indents, which temperature is suitable for cultivation, in particular incubation of said at least two microscopic objects.

Said heat source may be provided as a slide holder, which is adapted for matching said bottom surface profile at least corresponding to the contours of at least said at least two indents. Preferably said slide holder is provided as a heat conducting arm, preferably made of metal, such as aluminium, steel or the like.

In another system the bottom surface profile (23) of said device is provided with a heat conducting layer being adapted for connection to said heat source.

Said microscope may further comprise imaging means, such as camera or video equipment. The positioning means may further comprise
   at least one vertical hole extending through the slide holder;
   a light emitter, such as a laser providing a vertical light;
   a light sensor on the opposite side of the microscopy slide (2) relative to the light emitter for sensing the light being emitted, when the slide holder is in a correct position for microscopy.

The positioning means may further comprise a control unit for automatic positioning said device relative to said microscope and/or said heat source.

The control unit may furthermore be adapted for controlling the temperature of said heat source for a stable incubator environment, and/or adapted for monitoring and/or acquiring images of said microscopic objects using said imaging means, and/or analyzing said images for a quality assessment of said objects, and/or keeping a record of replacement slides.

In another embodiment the system further comprises means for performing non-invasive measurements of metabolic activity comprising micro sensors, for measuring e.g. pH, oxygen content and the like.

The system preferably comprises means for holding more than one device as described above, such as a slide holder capable of holding several devices, such as 4 or 6 devices.

The system is preferably a combination of a gas incubator, such as a tri-gas incubator, and a digital microscope for unattended image acquisition. The system can be viewed as an incubator with a build-in microscope or as a microscope with build-in incubator.

In a preferred embodiment the system comprises:
   1) Thermostated aluminium arm designed to fit the unique bottom topography of the polymer slides to ensure that the embryo is surrounded by heat conducting aluminium.
   2) Means having ability to perform non-invasive measurements of metabolic activity by using microsensors. One example is to measure oxygen respiration using oxygen microelectrodes of $CO_2$ concentration with pH microsensors. Accurate positioning of the sensors is ensured by a tiny hole in the slide holder, and a vertical laser illuminating the sensor tip. The slide holder is moved horizontally until the sensor tip is illuminated by laser light coming though the hole, then the X-Y coordinates of the slide holder is measured. Then the slide holder is moved until the tiny hole is centred in the field of view of the camera system and the new X-Y coordinates are measured. The difference in coordinates between the two observations is a measure of the offset between camera and sensor tip. The offset can then be used to move visible objects centred in the camera field of view to the sensor tip. I.e. by using the offset it is possible to unattended move objects of interest from the image acquisition position to the microsensor profiling position.

3) Means capable of handling more than one device (i.e. organisms/cells/embryos from more than one patient at the time). The present invention will easily handle four or five different slides with a total of 48 to 60 organisms.

4) Control software which unattended monitors the organisms, acquires and analyzes the images and provides a quality assessment of the organisms within. The software accepts addition of new dishes and termination of others without affecting ongoing measurements.

The software used may for example comprise the methods as described in WO 2007/042044 and WO 2007/144001.

In an automated system for monitoring objects being positioned in the depressions of the device it is of importance to be able to position the microscope and acquire images of the objects several times without losing track of each object, ie. it is important that each object may be uniquely identified for each period of monitoring and acquisition of images, in order to provide information of any changes in the objects. Therefore, in yet a further embodiment the invention relates to a device for monitoring and/or culturing of at least two microscopic objects (1a, 1b) and object media (5a, 5b), comprising—a slide (2) comprising at least two depressions (3a, 3b) in a top surface (2A) thereof; wherein said slide comprises means for uniquely identifying each depression. It is preferred that the unique identification is machine-readable, and furthermore it is preferred that the unique identification may be registered automatically.

Since a microscope is used for imaging the objects then it is preferred that the unique identification is readable at the magnification used for imaging the objects. Accordingly, it is preferred that the unique identification for each depression is less than 1.5 mm, such as 1 mm or less. Even more preferred the unique identification is arranged so that it may be imaged in the same image field as the microscopic object to which it relates.

The means for uniquely identifying each depression may be accomplished in several ways:

- by providing the device with positioning means so that it may either be positioned in only one unique position in relation to the microscope and camera, for example a recess or a protruding part capable of engaging a corresponding part of a slide holder, or that the positioning means comprises markers on the slide, whereby the position of each depression is determined relative to said marker
- by providing X-Y position information on the slide, such as at least one marker for identifying a row of depressions and at least one marker for identifying a column of depressions at said slide
- by providing individual identification markers in relation to each depression, such as individual indent identification (41) in and/or upon said substantially planar bottom surface of the indent and/or in and/or upon said bottom surface profile and/or within said transparent bottom part of said indent.

Figure 11A:
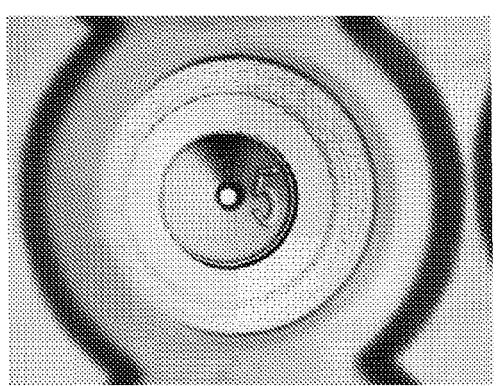
FIG. 11A, 11B are top view images of a device according to the invention further comprising individual indent identification ID in a depression and/or indent, for one depression and for six depressions, respectively.
Figure 11B:
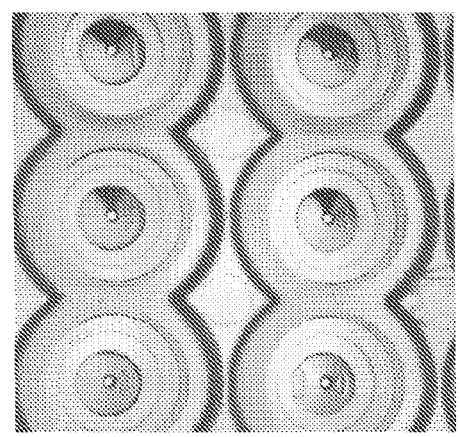

As shown in FIGS. 11A and 11B, showing top side images of parts of a slide or device according to the invention, there may further be provided individual indent identification 41, in the form of printed, moulded or cut letters, symbols or numbers in and/or upon said substantially planar bottom surface of the indent and/or in and/or upon said bottom surface profile and/or within said transparent bottom part of said indent and/or said depression.

Selection or identification of embryos. The present invention further enables a application for selecting an embryo for transplantation. The method implies that the embryo has been monitored with the method for determining a change in the embryo as described above in order to determine when cell divisions have occurred and optionally whether cell death has occurred as well as the quality of cell divisions and overall quality of embryo. It is preferred to select an embryo having substantially synchronous cell division giving rise to sharp extremas in the difference images, and more preferred to select an embryo having no cell death.

The selection or identifying method may be combined with other measurements as described above in order to evaluate the quality of the embryo. The important criteria in a morphological evaluation of embryos are: (1) shape of the embryo including number of blastomers and degree of fragmentation; (2) presence and quality of a zona pellucida; (3) size; (4) colour and texture; (5) knowledge of the age of the embryo in relation to its developmental stage, and (6) blastomere membrane integrity.

The dimensions of each depression (3a, 3b) and/or indent (4a, 4b) may be adapted to the application selected.

In one embodiment the system arranged for performing microscopy and/or culturing of at least two microscopic objects comprises a device for handling at least two microscopic objects and object media, said device comprising a microscopy slide comprising at least two depressions in a top surface thereof; each depression comprising an indent of a smaller cross section than the depression for holding each respective microscopic object and object media, wherein at least said indents exhibit a bottom surface profile corresponding to the contours thereof upon said slide; wherein said system is further provided with positioning means comprising a slide holder, which is adapted for matching said bottom surface profile at least corresponding to the contours of at least said at least two indents.

The tight fit between the matching contours of the slide and the slide holder ensure easy positioning of slide with µm accuracy as it settles in holder. Unattended microscopy is therefore possible even after removal and re-insertion of the slide. hus, positioning microscopic objects in such a slide in defined spots that can be routinely inspected, manipulated and/or photographed automatically.

In a further aspect the invention relates to a method for handling a device as described above, comprising the step of positioning said device within a system according to by matching said bottom surface profile (20) of said device at least corresponding to the contours of at least said at least two indents to corresponding positioning means comprising a slide holder of said system.

Furthermore, the invention relates to a method for microscopy and/or cultivation of objects in a device as described above in a system, comprising the step of positioning the device under the microscope and/or the heat source suitable for providing temperatures for culturing said at least two microscopic objects (1a, 1b) relative thereto.

In one embodiment the method further comprises the step of matching said bottom surface profile (20) of said device at least corresponding to the contours of at least said at least two indents to corresponding positioning means comprising a slide holder of said system. The step of matching may be performed by holding the top surface of the microscopy slide substantially horizontally and moving the slide to a position above the slide holder and descending the slide vertically down over said slide holder.

The step of performing microscopy of said at least two microscopic objects (1a, 1b) may be performed either manually or automatically, and either subsequently or substantially at the same time.

The step of providing the temperature for culturing preferably provides a given stable temperature to at least said indents by connecting said heat conducting layer to said heat source, which temperature is suitable for cultivation, in particular incubation of said at least two microscopic objects. Said heat source may be connected to said slide, said slide holder, and/or said protrusion.

The method may further comprise the step of providing the heat conducting layer with a predetermined temperature suitable for cultivation over a certain time period.

The method may further comprise the step of providing object media (5a, 5b) in at least each of said indents (4a, 4b) in such a way that said media (5a, 5b) is not in mutual fluid communication;

providing a microscopic object (1a, 1b) in each of said at least two indents (4a, 4b);

providing a common overlaying layer (7) within said at least one reservoir (6) in such a way that said media (5a, 5b) is not in mutual fluid communication; and performing microscopy and/or cultivation of said at least two microscopic objects.

The common overlaying layer may be fluid, semisolid and/or solid, and preferably fluid during cultivation temperatures. Furthermore, the object media may be fluid, semisolid and/or solid, and preferably fluid during cultivation temperatures.

The microscopic objects (1a, 1b) are for example microscopic organisms, such as growing cell cultures, in particular developing embryos. In a preferred embodiment the microscopic organisms are selected from the group containing in vitro cell cultures, such as single cell cultures, embryos such as oocytes, embryos, protoblasts, cytoblasts, etc., and/or bacteria, biological samples, and any combination thereof.

The step of positioning said device is preferably performed by manual and/or automated positioning by manipulating said handling protrusion (70) and/or said slide holder in the X, Y, and/or Z-direction. Accordingly, in one embodiment the positioning step further comprises automatically positioning said device relative to said microscope and/or said heat source using said control unit, such as wherein the positioning step further comprises emitting a light, such as a laser light for providing at least one vertical light beam, positioning said slide relative to said microscope and/or said heat source until said at least one light beam is passing through said at least one vertical hole extending through the slide holder and is sensed by said sensor on the opposite side of the microscopy slide.

The methods according to the invention may further comprise the step of monitoring and/or providing images of said slide using said camera and/or video equipment, such as described above and described in WO 2007/042044 and WO 2007/144001.

Furthermore, the methods according to the invention may comprise a step of measuring the offset between camera and a sensor tip.

In another embodiment the method according to the invention may further comprise the step of controlling the temperature of said heat source for a stable incubator environment, and/or the step of monitoring and/or acquiring images of said microscopic objects using said imaging means, and/or analyzing said images for a quality assessment of said objects, and/or keeping a record of replacement slides.

References

Articles

Holm P, Shukri N N, Vajta G, Booth P, Bendixen C and Callesen H (1998) *Developmental kinetics of the first cell cycles of bovine in vitro produced embryos in relation to their in vitro viability and sex*. Theriogenology 50: 1285-1299

Lundin K, Bergh C and Harderson T (2001) *Early embryo cleavage is a strong indicator of embryo quality in human IVF*. Hum Reprod 16, 2652-2657

The invention claimed is:

1. A device for monitoring and/or culturing of at least two microscopic objects and object media comprising:
a slide, the slide comprising:
at least two depression in a top surface thereof, each depression having a bottom surface profile, and
identification markers in the form of letters, symbols and/or numbers for uniquely identifying each depression, each identification marker having a height, wherein the height of each of the identification markers is less than 1.5 mm, wherein each depression comprises an indent of a smaller cross-section than the depression for containing at least one of the microscopic objects and object media, the indent having a bottom part and a bottom surface of the bottom part and wherein the identification markers provided individual indent identification in or upon the bottom surface profile of the depression and/or in or upon the bottom surface of the indent bottom part.

2. The device according to claim 1, wherein the height of each of the identification markers is less than 1 mm.

3. The device according to claim 1, wherein the identification markers comprise at least one positioning marker at the slide.

4. The device according to claim 3, wherein the at least one positioning marker is a recess or a protruding part adapted to engage a corresponding part on a slide holder.

5. The device according to claim 1, wherein the identification markers comprise at least one marker for identifying a row of depressions and at least one marker for identifying a column of depressions at the slide.

6. The device according to claim 1, wherein said identification markers have a size adapted such that the elements are readable in a microscope.

7. The device according to claim 1, wherein the one or more individual identification markers are arranged such that at least one of the one or more individual identification markers can be imaged in the same microscopic image field as one of the at least two microscopic objects.

8. The device according to claim 1, wherein the identification markers are machine readable.

9. The device according to claim 1, wherein the identification markers comprise letters, symbols and/or numbers which are printed onto, or molded or cut into the slide.

10. The device according to claim 1, wherein the bottom part of each indent is planar.

11. The device according to claim 1, wherein the bottom part of each indent is transparent.

12. The device according to claim 1, wherein the identification markers consist of one or more microscopic numerals placed close to the indent so that the one or more microscopic numerals can be seen in a microscope during handling of the microscopic objects.

13. The device according to claim 1, wherein each depression further comprises a substantially smooth bottom part in the form of a funnel for directing at least one of the at least two microscopic objects into the indent, the funnel having a horizontal sectional cut selected from the groups consisting of: circular, elliptical, rectangular, harlequin and hexagonal.

14. The device according to claim 1, wherein the indent and the depression each have a diameter, and wherein the indent diameter is smaller than the depression diameter.

15. The device according to claim 1, wherein the indent has a diameter and each of the microscopic objects has a diameter, and wherein the indent diameter is 1.1 to 10 times the diameter of each of the microscopic objects, or 1.5 to 3 times the diameter of each of the microscopic objects.

16. The device according to claim 1, wherein the depressions and/or the indents have a bottom surface profile corresponding to the contours thereof upon the slide; and wherein the topography of said bottom surface profile is adapted to match a corresponding topography of a slide holder.

17. The device according to claim 1, wherein at least a part of the device is provided with a handling protrusion.

18. The device according to claim 1, wherein the microscopic objects are microscopic organisms.

19. The device according to claim 1, wherein the microscopic objects are growing cell cultures.

20. The device according to claim 1, wherein the microscopic objects are embryos.

\* \* \* \* \*